United States Patent
Baron et al.

(10) Patent No.: US 7,994,381 B2
(45) Date of Patent: Aug. 9, 2011

(54) WOUND COVERING AND PRODUCTION PROCESS

(75) Inventors: Catherine Baron, Meyenheim (FR); Alfred Rasche, Dormagen (DE); Fabian Leuthard, Merenschwand (CH); Adrian Schulthess, Tentlingen (CH); Andreas Dobmann, Oberkirch (CH); Manuel Leumann, Beinwil am See (CH); Dirk Clasen, Beckdorf-Nindorf (DE)

(73) Assignee: Collano AG, Sempach-Station (CH)

( * ) Notice: Subject to any disclaimer, the term of this patent is extended or adjusted under 35 U.S.C. 154(b) by 902 days.

(21) Appl. No.: 11/928,364

(22) Filed: Oct. 30, 2007

(65) Prior Publication Data
US 2008/0107718 A1 May 8, 2008

(30) Foreign Application Priority Data
Nov. 7, 2006 (EP) ..................... 06123627

(51) Int. Cl.
*A61F 13/00* (2006.01)
*B29D 7/00* (2006.01)
*B29C 65/00* (2006.01)

(52) U.S. Cl. .................... 602/41; 264/45.9; 156/256

(58) Field of Classification Search ........... 602/41–46, 602/54, 55; 24/304; 264/45.9, 46.4, 173.11, 264/173.12, 173.16; D24/189; 128/848, 128/888–889; 156/1, 60, 325, 326, 327, 156/330.9, 331.1, 331.4
See application file for complete search history.

(56) References Cited

U.S. PATENT DOCUMENTS

| | | | |
|---|---|---|---|
| 3,551,243 A * | 12/1970 | Schuur et al. ............ 156/244.14 |
| 3,668,050 A | 6/1972 | Donnelly | |
| 5,147,338 A * | 9/1992 | Lang et al. ............ 604/304 |
| 6,165,625 A | 12/2000 | Sommers et al. | |
| 6,191,216 B1 | 2/2001 | Ganster et al. | |
| 6,245,271 B1 * | 6/2001 | Jacobs et al. ............ 264/154 |
| 2005/0019560 A1 | 1/2005 | Hesse et al. | |
| 2010/0222730 A1 * | 9/2010 | Leumann et al. ............ 602/46 |

FOREIGN PATENT DOCUMENTS

| | | |
|---|---|---|
| EP | 651984 | 5/1995 |
| EP | 897406 | 2/1999 |
| EP | 1469052 | 10/2007 |
| WO | 91/01706 | 2/1991 |
| WO | 95/15135 | 6/1995 |

OTHER PUBLICATIONS

An description of polyol from huntsman.com.*
Stokes; "Joining Methods for Plastics and Plastic Composites: An Overview"; Polymer Engineering and Science; Mid-Oct. 1989; vol. 29, No. 19; pp. 1310-1324; XP-002418754; New York.
"Desmodur E 305"; Bayer Material Science; Edition May 9, 2005 (replaces edition dated Aug. 12, 2004); pp. 1-2; XP-002419598; Leverkusen, Germany (and translation).
"Desmodur/Desmophen for Coatings" Products and Properties Commercial Products brochure; Bayer Material Science; Edition May 2004; XP-002419597; Leverkusen, Germany (and translation).

* cited by examiner

*Primary Examiner* — Patricia M Bianco
*Assistant Examiner* — Tarla R Patel
(74) *Attorney, Agent, or Firm* — Shoemaker and Mattare

(57) ABSTRACT

The invention relates to a production process for a foam wound dressing having an external germ barrier, more particularly a film layer, and also to a wound dressing thus obtained, having, where appropriate, a pressure-sensitive adhesive layer. In the process according to the invention the germ barrier is produced by means of extrusion directly on the foam base. This results in a more reliable bond between foam layer and germ barrier, without detriment to the absorptiveness of the foam for wound exudate. The process presented is simple and cost-effective, and all of the requirements from the medical sector (e.g. absence of solvent) can be met.

17 Claims, 2 Drawing Sheets

WOUND COVERING AND PRODUCTION PROCESS

Figure 1:
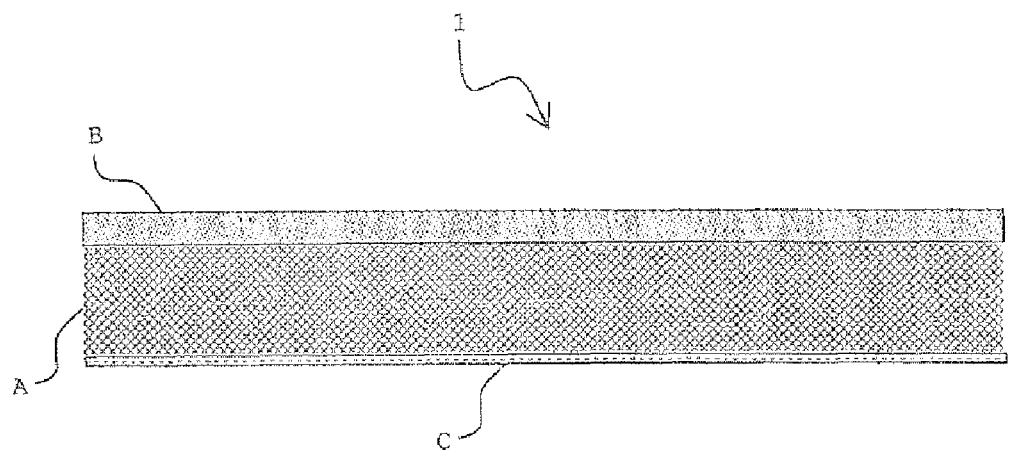

The invention concerns the field of wound coverings based on foam materials, and more particularly production processes for such wound coverings.

Wound coverings are intended to fulfil a multiplicity of functions, including, for example, the assurance of imperviousness to germs and the establishment of a physiological healing environment, with a moist healing environment nowadays being preferred for secondarily healing wounds. The wound covering ought, moreover, not to be cytotoxic or allergenic, and ought to be able to be removed/changed without trauma. A further requirement is that excessive exudate must be led away from the wound.

Foam-based wound coverings are being used increasingly nowadays in wound care, more particularly for chronic wounds. Foam wound coverings of this kind have the advantage that exudate can be removed reliably from the wound through the absorbency of the foam. As compared with their established counterparts such as gauze bandages, muslin bandages, etc., foam-based wound coverings thus offer the advantage of a higher absorption capacity for exudate, plus the further advantage that there is no sticking to the wound and hence that the dressing can be changed painlessly.

On the side facing away from the wound, these foam wound coverings are generally covered with a germ barrier, typically a film. This germ barrier on the one hand represents protection against bacteria forcing their way in, and, furthermore, also regulates gas exchange with the ambient environment. Through controlled adjustment of the water vapour transmission rate through this germ barrier it is possible to ensure that a sufficiently moist microclimate prevails beneath the wound covering, without maceration of the skin. Moreover, this germ barrier protects clothing and other dressing material from emergent wound exudate.

At the present time germ barriers of this kind, films for example, are bonded to the foam base by applying either solvent-based adhesives (typically by spraying) or else hot-melt adhesives. In these cases the adhesive may be applied either to one side (typically to the film) or to both sides, in other words to the film and to the foam. An alternative option, for example, is to insert a heat-activatable adhesive nonwoven between film and foam, thereby producing the bond. Using an adhesive, however, it is always necessary to produce an interlayer in order to assure the join between foam and film.

A critical point in this connection in every case is that the adhesive layer must not hinder the transport of water vapour; generally speaking, the transmission rate ought to be more than 1000 g/m$^2$/day. A transmission rate of this kind can be achieved, for example, by way of an open coating pattern with adhesive, or by means of a film of adhesive which, though applied over the full area, is permeable to water vapour.

Assuring sufficient water vapour transmission rate through the adhesive layer during production is a not inconsiderable problem in practice, whereas transmission through the film and the foam can be determined and set using simple routine experiments. Moreover, the need for an adhesive layer makes production more expensive overall. In addition, joining film and foam with an adhesive layer is often unconvincing in practice, since there are continual instances of detachment of the film from the foam.

U.S. Pat. No. 5,147,338 discloses the spray application of a polyurethane film to a polyurethane foam in a wound covering. This allows the aforementioned adhesive layer to be omitted. The spray application of a polyurethane film to the foam, however, has a multiplicity of disadvantages. Firstly, uniform application is difficult to ensure. Secondly, there is significant penetration of the sprayed-on polyurethane material into the foam, which may considerably reduce the capacity of the foam to absorb wound exudate. Moreover, in order to ensure sprayability on the part of polyurethane materials, solvents must be added; solvent residues in the wound covering, however, are intolerable.

U.S. Pat. No. 3,668,050 discloses a surgical drape having an opening for surgery. The drape can have a film layer extruded onto a foam material. The foam material is located on the side facing away from the wound and has the function, among others, of preventing surgical instruments placed on it from slipping.

EP 651 984 discloses a plaster having an external non-porous film layer and a body-facing pressure-sensitive adhesive layer embedded within which there is a porous layer composed, for example, of foam with a thickness in the range from 0.01 to 0.5 mm. In this arrangement, the pressure-sensitive adhesive penetrates through to the external film layer; as a result of the embedding of the porous layer, the attachment of the pressure-sensitive adhesive to the plaster is stronger.

Frequently it is desired to provide the wound covering on the wound side with a pressure-sensitive adhesive layer, in order to prevent the wound covering from slipping. To be suitable for this purpose, a pressure-sensitive adhesive ought to have both a high water vapour transmission rate and, preferably, a low level of water absorption.

It is an object of the present invention, therefore, to avoid the disadvantages of the prior art, and more particularly to provide a foam wound covering, a production process for a foam wound covering, and a pressure-sensitive adhesive suitable for such a foam wound covering, the process being simple and cost-effective to implement, containing or leaving no residues (e.g. solvent residues) in the finished product, and thus ensuring an outstanding and robust bond between foam and film without lowering the absorption capacity of the foam for wound exudate.

This object is achieved by a wound covering, a process for producing such a wound covering, and a pressure-sensitive adhesive specifically suitable for such a wound covering, as defined in the claims.

The wound covering of the invention comprises a preferably solvent-free pressure-sensitive adhesive layer comprising a polymer which is obtainable by polymerizing at least one aromatic or, preferably, aliphatic isocyanate component with at least one diol or polyol component, preferably a polyester polyol or polyether polyol;

where a layer, more particularly an uninterrupted layer, of the pressure-sensitive adhesive has for a basis weight of approximately 100 g/m$^2$ a water vapour transmission rate of $\geq$2000 g/m$^2$/24 h, preferably of $\geq$2500 g/m$^2$/24 h, more preferably of $\geq$3000 g/m$^2$/24 h; and/or a water absorption of <5% by weight, preferably of <3.5% by weight, more preferably of <2% by weight.

The process for producing an at least two-layer article, more particularly a substantially uninterruptedly sheetlike article, more particularly still a wound covering, comprising a first layer composed of a foam material, exhibiting a first major surface and more particularly a second major surface; and a second layer as a germ barrier, more particularly composed of a film material, this second layer directly adjoining the first major surface of the first layer, comprises the following steps:

providing the foam material of the first layer, more particularly in a thickness between 1 mm to 10 mm, preferably between 3 mm to 5 mm;

applying, more particularly extruding, at least one thermoplastic material to the major surface of the foam material at a temperature above the softening temperature of the thermoplastic material, which material is subsequently solidified to give the second layer.

In this arrangement, the first layer composed of a foam material is preferably not embedded into a pressure-sensitive adhesive layer, hence in contrast to aforementioned document EP 651 984.

Alternatively and/or additionally it is likewise possible in the context of the invention to heat the first layer composed of a thermoplastic foam material to a temperature above the softening temperature. Thermoplasticity of the material for the second layer is then not a mandatory requirement. A disadvantage associated with methods involving heating the foam material, however, is that combining it with the second layer then takes place under pressure, which, in the case of inadequate boundary conditions to the operation, could adversely affect the structure of the heated foam material and hence, possibly, the capacity to absorb wound exudate and the water vapour transmission rate.

The two "major surfaces" of the foam material of the first layer are understood here to be those surfaces which, in the course of as-intended use as a wound covering, run substantially parallel to the covered skin surface of the injured person, both on the wound-remote side and on the wound-facing side.

Areas of the multi-layer material of the invention that are "substantially uninterrupted" are understood as being those areas which do not have any openings that would run significantly counter to the establishment of the desired moist environment beneath the wound covering in the course of as-intended use. The criterion "substantially uninterruptedly", in other words, does not rule out the presence, for example, of appropriately dimensioned perforation lines allowing sections to be separated off by tearing.

Surprisingly it has emerged that, particularly as a result of the extrusion of the germ barrier, preferably of a film material, directly (in other words without an interlayer of adhesive) onto the foam material, it is possible to produce wound coverings which exhibit not only outstanding strength on the part of the assembly but also only minimal penetration of the germ barrier material or film material into the foam. The absorption capacity of the foam is therefore not adversely affected, in the way observed, in contrast, in the case of sprayed-on film material. The material for producing the germ barrier need not be present in solution for extrusion (in contrast to the spraying technology), and, consequently, there are no residues of solvents at all in the finished product. Furthermore, production is easy to operate; the thickness of the applied layer can be set reliably and kept constant using conventional extrusion lines (particularly those with common slot dies). With appropriately chosen operating conditions, moreover, it is possible, alternatively or additionally, to employ processes other than extrusion, examples being flame lamination, calendering, ultrasonic welding, etc. Suitable processes are familiar per se to the skilled person. In the context of the present invention it must be ensured in any case that the operating conditions are chosen such that the above-described requirements relating to the absorption capacity of the foam material of the first layer for the wound exudate, the water vapour transmission rate of both layers, and the germ barrier property of the second layer are not detrimentally affected.

In other preferred embodiments of the invention the foam material provided is a polyurethane foam. The foam material provided is preferably hydrophilic. With further preference the foam material is substantially open-celled. An average pore size in the range from 0.02 mm to 0.2 mm can be selected with preference. Suitable and particularly preferred hydrophilic, polyurethane-based foam materials are known to the skilled person and available on the market (for example type Vivo MCF 03 from Corpura B.V., 4879 NE Etten-Leur, The Netherlands; or type 3014 of Polymer Health Technology, Ebbw Vale, NP23 8XE, United Kingdom).

In another advantageous embodiment of the invention the foam material is provided in a thickness between 1 mm to 10 mm, preferably between 3 mm and 5 mm. Such thicknesses have proved to be an outstanding compromise between the requisite absorption capacity for wound exudate and the handleability of the wound covering.

In particularly advantageous embodiments of the invention the at least one material is extruded in step b) onto the foam material in such a way as to form a second layer having a thickness between 10 μm to 500 μm, preferably 20 μm to 200 μm; typically 15 μm to 100 μm, preferably 20 μm to 40 μm. Thicknesses within the stated ranges have little or no effect on the handleability of the wound covering, and the aforementioned controlling of the water vapour transmission rate of the resulting film can be adapted in this thickness range to all of the requirements that occur in practice.

It has been found to be particularly advantageous that the extrusion of the at least one material in step b) takes place at a temperature in the range between 150° C. and 240° C., preferably between 180° C. and 220° C., more particularly between 200° C. and 210° C.

In a further, particularly preferred embodiment it is possible to produce two layers in step b), more particularly by extrusion of two materials, either sequentially or by means of coextrusion. Also possible is the application of a first film layer by means of extrusion and of a further layer by means, for example, of spraying. The invention makes it possible in particular to produce, for example, a thin, foam-facing layer which is optimized for adhesion to the foam; layer thicknesses of just 5 μm to 10 μm have proved to be sufficient for this purpose. It is then possible, as an external second layer, to apply a further layer possessing, for example, higher mechanical strength (typically in a thickness of about 10 μm to 20 μm), or to coextrude such a layer simultaneously. In this way, therefore, it is possible to produce, for example, film layers which are constructed from at least two part-layers, it being possible for the film layer overall to be very thin and yet to exhibit very good adhesion to the foam material and to have a soft hand. Moreover, the use of two different layers also makes it possible to control the water vapour transmission rate via the material selected for the additional layer, independently of the overall thickness of the film layer.

In a further embodiment of the invention the at least one material can be foamed during and/or after application, more particularly after the extrusion in step b). The foaming of a material during and/or after extrusion is familiar per se to the skilled worker and can be accomplished with conventional means (through the addition, for example, of a blowing agent such as azo-dicarbonamide, or by subsequent heat exposure). Advantageously it would be possible, for example, to extrude a first, foamed layer onto the foam, having a smaller pore size than the underlying foam layer. Subsequently (or else simultaneously, through coextrusion) the concluding layer, a film layer for example, can then be applied. As a result of the consequent decrease—not abrupt, but gradual—in porosity and/or transition from open-celled to closed-celled character, it is possible to obtain a further improvement in the adhesion between wound-facing foam and external film, also resulting, moreover, in a typically desired, visually smoother wound-remote face.

On the first layer, composed of a foam material, it is of course also possible, by extrusion, to produce a second, external layer as a germ barrier, composed of a foam material, and to do so, for example, without additional external (film) layer or layers. If, therefore, a foam is employed as a germ barrier, the foam in question must be a suitable, substantially closed-cell foam, in order to ensure the germ barrier effect and also, in particular, to establish the desired moist environment beneath the wound covering. Producing a closed-cell foam by and/or after extrusion is familiar to the skilled worker, as set out above. Any boundary conditions of the extrusion and/or of the heat treatment that may require adaptation can be determined easily by the skilled person in routine experiments.

With particular preference, after the extrusion of the material in step b), the extrudate is pressed against the first layer or the foam by means of a cooled roll. In this case, however, there is minimal penetration of the foam, if any, since the extrudate arrives on the foam in a preformed condition and, in particular, the viscosity of the melt is already very high indeed.

Further preference is given to providing a thermoplastic polyurethane material in step b), more particularly a polyether polyurethane. Thermoplastic polyether polyurethanes with approval for the medical sector are known to the skilled worker and available on the market. Particularly suitable thermoplastic materials have a melt flow index (MFI) to ISO 1133 of between 5 and 50 g/10 min at 170° C. and a piston weight of 21.6 kg.

With further advantage a wound-compatible pressure-sensitive adhesive can be applied at least partly to the second major surface of the first layer on the wound side. The pressure-sensitive adhesive in this case must have a low level of adhesion set in such a way as to allow atraumatic removal from the wound (referred to as soft peel behaviour). In this case, in chemical terms, the pressure-sensitive adhesive is preferably such that it can be applied areally without affecting the water vapour transmission rate and the conduction of the wound exudate to an intolerable degree. Suitable layer thicknesses can easily be determined in this case by the skilled person, using routine experiments. Typical layer thicknesses are 5 µm to 500 µm; 10 µm to 200 µm are preferred. Excessively deep penetration into the foam must be avoided here at any rate, in order not to hinder the absorption of wound exudate. Alternatively the pressure-sensitive adhesive is applied only partially, preferably dotwise; the requisite permeability is in this case achieved via the pattern of application. The pressure-sensitive adhesive is preferably applied only in a marginal region of the wound covering, which attaches to the skin outside the wound region in the case of as-intended use. In this context, for example, a narrow strip or a grip tab may be provided at the margin of the wound covering, this strip or tab not being provided with pressure-sensitive adhesive and so permitting easy removal of the wound covering.

Types of pressure-sensitive adhesive which can be used for the aforementioned purposes are those compositions which are known per se to the skilled person, based for example on polyacrylate(s) (solvent-based, but preferably aqueous dispersions and/or, with particular preference, UV-(post)crosslinkable types); silicones (solvent-based, but preferably aqueous dispersions); ethylene-vinyl acetate; preferably with high vinyl acetate content; and also hydrocolloid adhesives, based for example on polyisobutylene (PIB), synthetic rubber or else polyacrylate(s). Pressure-sensitive adhesive types of this kind are described in detail per se in the literature, as for example in the Handbook of Pressure Sensitive Adhesive Technology, 2nd edition, Donatas Satas, 1989, Van Nostrand Reinhold, ISBN 0-442-28026-2.

In the context of the present invention it is preferred to use polyurethane pressure-sensitive adhesives, of the kind likewise described in the aforementioned Handbook of Pressure Sensitive Adhesive Technology and also, for example, in EP 897 406 (hexamethylene diisocyanate-based). In contrast to the polyurethane pressure-sensitive adhesives described in EP 897 406, however, adhesives based on isophorone diisocyanate have emerged as being particularly advantageous in the context of the present invention; these polyurethane pressure-sensitive adhesives unexpectedly possess a particularly high water vapour transmission rate in conjunction with very low water absorption.

The invention accordingly further relates to a pressure-sensitive adhesive for use on an at least two-layer, substantially uninterruptedly sheetlike article as described above, more particularly for use on a wound covering as described above. The solvent-free pressure-sensitive adhesive comprises a polymer which is obtainable by polymerizing at least one aromatic or, preferably, aliphatic isocyanate component with at least one diol or polyol component, preferably a polyester polyol or polyether polyol, a layer of the pressure-sensitive adhesive, more particularly an uninterrupted layer, having for a basis weight of approximately 100 g/m² a water vapour transmission rate of $\geq$2000 g/m²/24 h, preferably of $\geq$2500 g/m²/24 h, more preferably of $\geq$3000 g/m²/24 h; and/or a water absorption of <5% by weight, preferably of <3.5% by weight, more preferably of <2% by weight. In particularly preferred embodiments the solvent-free pressure-sensitive adhesive comprises a polymer which is obtainable by polymerizing isophorone diisocyanate (or a modified isophorone diisocyanate) with at least one diol or polyol component.

The following can be used as ingredients of the pressure-sensitive adhesive:

Diol or Polyol Compounds

The following can be employed: oxyalkyl polymers, preferably polyether polyols having 2, 3, 4, 5 or 6 hydroxyl groups, OH numbers of 20 to 112, and an ethylene oxide content of $\geq$10% by weight, preferably 10% to 40% by weight, more preferably 10% to 20% by weight, polyacrylic polyols, polyester polyols, polyolefin polyols, polythiol polyols, and polyamine compounds. The glass transition temperatures here ought to be very low indeed, in other words below about 20° C., preferably below about 0° C., more preferably below about −10° C.

Polyether polyols having molecular weights between 600 and 12 000 are preferred and can be obtained by known processes such as, for example, by reaction of starter compounds having a reactive H atom with alkylene oxides (for example ethylene oxide and/or propylene oxide, preferably propylene oxide, butylene oxide, styrene oxide, tetrahydrofuran or epichlorohydrin or mixtures of two or more thereof). It is likewise possible to employ tetramethylene ether glycols. Likewise possible are further modifications, with monoethylene glycol (MEG), dipropylene glycol (DPG), trimethylolpropane (TMP), for example. Nowadays preferred for use in medicine are aliphatic polyether polyols.

Examples of suitable starter compounds include water, ethylene glycol, propylene 1,2- or 1,3-glycol, butylene 1,4- or 1,3-glycol, hexane-1,6-diol, octane-1,8-diol, pentane-1,5-diol, heptane-1,7-diol, and their higher homologues, neopentyl glycol, 1,4-hydroxymethyl-cyclohexane, 2-methyl-1,3-propanediol, glycerol, trimethylolpropane, 2,2-(bis-4,4'-hydroxyphenyl)propane, trimethylolpropane, glycerol or pentaerythritol, hexane-1,2,6-triol, butane-1,2,4-triol, trimethylolethane, mannitol, sorbitol, methylglycosides, sugars, phenol, isononylphenol, resorcinol, hydroquinone, 1,2,2- or 1,1,2-tris(hydroxyphenyl)ethane, ammonia, methylamine, ethylenediamine, tetra- or hexamethylenamine, triethanolamine, aniline, phenylenediamine, 2,4- and 2,6-diaminotoluene and polyphenylpolymethylenepolyamines, of the kind obtainable by aniline-formaldehyde condensation, or mixtures of the aforementioned starter compounds.

Likewise suitable as diol or polyol component are polyacrylates which carry OH groups. These polyacrylates are obtained, for example, by polymerizing ethylenically unsaturated monomers which carry an OH group. Such monomers are obtainable, for example, through the esterification of ethylenically unsaturated carboxylic acids and difunctional alcohols, the alcohol generally being present in a slight excess. Examples of unsaturated carboxylic acids of this kind are acrylic acid, methacrylic acid, crotonic acid or maleic acid. Examples of corresponding OH-carrying esters are 2-hydroxyethyl acrylate, 2-hydroxyethyl methacrylate, 2-hydroxypropyl acrylate, 2-hydroxypropyl methacrylate, 3-hydroxypropyl acrylate or 3-hydroxypropyl methacrylate, or mixtures of two or more thereof.

Likewise suitable as a diol or polyol component are polyester polyols, more particularly those having a molecular weight of about 200 to about 10 000. Thus, for example, it is possible to use polyester polyols formed by reaction of low molecular weight alcohols, more particularly of ethylene glycol, diethylene glycol, neopentyl glycol, hexanediol, butanediol, propylene glycol, glycerol or trimethylolpropane, with caprolactone. Likewise suitable as polyfunctional alcohols for preparing polyester polyols are 1,4-hydroxy-methylcyclohexane, 2-methyl-1,3-propanediol, butane-1,2,4-triol, triethylene glycol, tetraethylene glycol, polyethylene glycol, dipropylene glycol, polypropylene glycol, dibutylene glycol and polybutylene glycol. Further suitable polyester polyols can be prepared by polycondensation. Thus difunctional and/or trifunctional alcohols can be condensed with a substoichiometric amount of dicarboxylic acids and/or tricarboxylic acids, or their reactive derivatives, to form polyester polyols. Suitable dicarboxylic acids are, for example, adipic acid or succinic acid and their higher homologues having up to 16 C atoms, and also unsaturated dicarboxylic acids such as maleic acid or fumaric acid, and also aromatic dicarboxylic acids, more particularly the isomeric phthalic acids, such as phthalic acid, isophthalic acid or terephthalic acid. Examples of suitable tricarboxylic acids include citric acid and trimellitic acid. The stated acids can be used individually or as mixtures of two or more thereof. Particularly suitable polyester polyols are those formed from at least one of the said dicarboxylic acids and glycerol and having a residual OH group content. Particularly suitable alcohols are hexanediol, ethylene glycol, diethylene glycol or neopentyl glycol, or mixtures of two or more thereof. Particularly suitable acids are isophthalic acid or adipic acid or their mixtures. Polyester polyols with a high molecular weight, more particularly in the region of >5000 g/mol, include, for example, the reaction products of polyfunctional, preferably difunctional, alcohols (together where appropriate with small amounts of trifunctional alcohols) and polyfunctional, preferably difunctional, carboxylic acids. Instead of free poly-carboxylic acids use may also be made (when possible) of the corresponding polycarboxylic anhydrides or corresponding polycarboxylic esters with alcohols having preferably 1 to 3 C atoms. The polycarboxylic acids may be aliphatic, cycloaliphatic, aromatic or heterocyclic. They may, where appropriate, be substituted, for example by alkyl groups, alkenyl groups, ether groups or halogens. Examples of suitable polycarboxylic acids include succinic acid, adipic acid, suberic acid, azelaic acid, sebacic acid, phthalic acid, isophthalic acid, terephthalic acid, trimellitic acid, phthalic anhydride, tetrahydrophthalic anhydride, hexahydrophthalic anhydride, tetrachlorophthalic anhydride, endomethylene-tetrahydrophthalic anhydride, glutaric anhydride, maleic acid, maleic anhydride, fumaric acid, dimer fatty acid or trimer fatty acid, or mixtures of two or more thereof. Where appropriate it is possible for minor amounts of monofunctional fatty acids to be present in the reaction mixture. The polyesters may where appropriate have a small fraction of carboxyl end groups. Polyesters obtainable from lactones, epsilon-caprolactone for example, or from hydroxycarboxylic acids, omega-hydroxycaproic acid for example, may likewise be employed.

It is also possible to mix the aforementioned diols or polyols. In this case account must be taken of their compatibility. In the medical sector it is preferred to use aliphatic polyester polyols.

Isocyanates

Examples of suitable polyisocyanates according to the invention are MDI (diphenylmethane diisocyanate), TDI (tolylene diisocyanate), XDI (xylene diisocyanate), NDI (naphthalene diisocyanate), phenylene diisocyanate, dicyclohexylmethane diisocyanate, butane 1,4-diisocyanate, tetramethoxybutane 1,4-diisocyanate, hexane 1,6-diisocyanate, ethylene diisocyanate, 2,2,4-trimethylhexamethylene diisocyanate, ethylethylene diisocyanate, dicyclohexylmethane diisocyanate, 1,4-diisocyanatocyclohexane, 1,3-diisocyanatocyclohexane, 1,2-diisocyanatocyclohexane, 1,3-diisocyanatocyclopentane, 1,2-diisocyanatocyclopentane, 1,2-diisocyanatocyclobutane, 1-isocyanatomethyl-3-isocyanato-1,5, 5-trimethylcyclohexane (isophorone diisocyanate, IPDI), 1-methyl-2,4-diisocyanatocyclohexane, 1,6-diisocyanato-2, 2,4-trimethylhexane, 1,6-diisocyanato-2,4,4-trimethylhexane, 5-isocyanato-1-(2-isocyanatoeth-1-yl)-1,3,3-trimethylcyclohexane, 5-isocyanato-1-(3-isocyanatoprop-1-yl)-1,3,3-trimethylcyclohexane, 5-isocyanato-1-(4-isocyanato-but-1-yl)-1,3,3-trimethylcyclohexane, 1-isocyanato-2-(3-isocyanatoprop-1-yl)-cyclohexane, 1-isocyanato-2-(2-isocyanatoeth-1-yl)-cyclohexane, 2-heptyl-3,4-bis-(9-isocyanatononyl)-1-pentyl-cyclohexane, norbornane diisocyanatomethyl, chlorinated, brominated, aliphatic or alicyclic diisocyanates containing sulphur or containing phosphorus, and derivatives of these diisocyanates, more particularly dimerized or trimerized types. Aliphatic compounds are preferred in the medical sector. One particularly preferred embodiment uses isophorone diisocyanate, which allows very good water vapour transmission rates in conjunction, in particular, with low water absorption.

Prepolymers

Polyurethane prepolymers can be employed. Generally speaking, the polyurethane prepolymers which can be used in the context of the present invention have a molecular weight of about 500 g/mol to about 15 000 g/mol, preferably about 500 g/mol to about 10 000 g/mol, more preferably about 700 g/mol to about 4500 g/mol.

Additives

Where appropriate the PU composition of the invention may further comprise additives such as, for example, plasticizers, stabilizers such as antioxidants or photostabilizers, tackifiers, colourants, fillers, thickeners and rheological additives.

Plasticizers:

Plasticizers used are, more particularly, phthalic acid derivatives, or phthalic esters which have 6 to 12 carbon atoms and have been esterified with a linear alkanol, an example being dioctyl phthalate. Polyethylene glycols and their derivatives, vegetable and animal oils, such as glycerol esters of fatty acids and their polymerization products, and benzoate compounds (benzoate plasticizers), examples being sucrose benzoate, diethylene glycol dibenzoate and/or diethylene glycol benzoate, in which about 50% to about 95% of all the hydroxyl groups have been esterified, phosphate plasticizers, an example being tert-butylphenyl diphenyl phosphate, polyethylene glycols and their derivatives, examples being diphenyl ethers of poly(ethylene glycol), liquid resin derivatives, for example the methyl ester of hydrogenated resin, are likewise suitable as plasticizers. Particularly preferred are aliphatic diesters such as dinonyl adipate or dinonyl sebacate.

Stabilizers:

The stabilizers used in the context of the invention (antioxidants) include hindered phenols such as BHT, Irganox® 1010, 1076, 1330, 1520 (Ciba Speciality Chemicals) and also tocopherols. Particular preference is given to using vitamin E (alpha-tocopherol). It is like-wise possible to employ polyfunctional phenols and also sulphur- and phosphorus-containing compounds and/or 1,3,5-trimethyl-2,4,6-tris(3,5-di-tert-butyl-4-hydroxybenzyl)benzene; pentaerythritol tetrakis-3-(3,5-di-tertbutyl-4-hydroxyphenyl)propionate; n-octadecyl 3,5-(di-tert-butyl-4-hydroxylphenyl)propionate; 4,4-methylene-bis(2,6-di-tert-butylphenol); 4,4-thiobis(6-tert-butyl-o-cresol); 2,6-di-tert-butylphenol; 6-(4-hydroxyphenoxy)-2,4-bis(n-octylthio)-1,3,5-triazine; di-n-octadecyl 3,5-di-tert-butyl-4-hydroxybenzylphosphonates; 2-(n-octylthio)ethyl-3,5-di-tert-butyl-4-hydroxybenzoate; and sorbitol hexa[3-(3,5-di-tert-butyl-4-hydroxyphenyl)propionate]. Suitable photostabilizers are for example, Tinuvin® products (Ciba Speciality Chemicals), benzotriazole compounds, salicylates, substituted tolyl and metal chelate compounds, preference being given to benzotriazole derivatives. Combinations of the abovementioned compounds are also possible. The amounts typically employed are between 0.1% and 10% by weight.

For the setting of certain properties of the pressure-sensitive adhesive it is possible to use further additives, in the manner customary in the art. These include, for example, colourants such as titanium dioxide, fillers such as talc, chalk, clay and the like. It is likewise possible to incorporate certain hydrophilic polymers, examples being PVOH (polyvinyl alcohol), polyvinylpyrrolidone, hydroxypropylcellulose, polyvinyl methyl ethers, and cellulose esters, especially their acetates with a low degree of substitution. These additives may enhance the wettability of the adhesives. By fillers are meant the fillers that are typically employed in polyurethane chemistry. These also include zinc oxide, titanium oxide and silica derivatives (e.g. Aerosils® (Degussa)). A further additive that may be mentioned, for example, are the short fibres with an organic or inorganic basis (e.g. glass fibres, textile fibres).

In order to enhance the wetting of the substrate it is possible to add typical wetting agents to the PU pressure-sensitive adhesive: examples are Poloxamers (copolymer of polyoxyethylene and polyoxypropylene), sorbitan esters, fatty acids such as Span® (Sigma-Aldrich), esters of polyoxyethylene-sorbitan and fatty acids, such as polysorbates or Polysorbate® (Spectrum Chemical), polyethoxylated hydrogenated castor oils such as Cremophor® (BASF), for instance, polyoxyethylene stearates, e.g. Myrj®, (Uniqema) or any combination of these wetting agents. Preferably the wetting agent is a polysorbate and vitamin E.

Tackifiers:

In addition it is possible for the pressure-sensitive adhesive to comprise tackifier resins. Natural, modified natural, and synthetic resins may be employed, typically having a molecular weight of up to 1500 g/mol. The compatibility of the resins with the other components must in each case be tested in routine experiments of the type customary in the art. Suitable by way of example are hydrocarbon resins, more particularly $C_5$ to $C_9$ resins, preferably $C_9$ resins modified with $C_5$ resins, and the like. All of the hydrocarbon resins may be partly hydrogenated or fully hydrogenated. Likewise employed are natural resins such as balsam resin or tall resin. The stated resins may also be esterified with corresponding polyfunctional alcohols such as pentaerythritol esters, glycerol esters, diethylene glycol esters, triethylene glycol esters or methyl esters, and employed in that form. Examples of known commercial products are "Staybelite" ster 10, "Foral" 85-105, "Hercolyn" D, "Alresen" 214 R, "Alresen" 191 R, "Alresen" 500 R 80 and "Cellolyn" 21 s. Polyterpene resins, and the terpene-phenolic resins, can likewise be included as tackifier resins in the formulation, as can the synthetic resins: ketone resins, coumarone resins and indene resins, and also hydrocarbon resins, are also possible, for example, under trade names such as "Ketonharz" N, "Lutonal" J 30, "Lutonal" J 60, "Vinnapas" B 17, "Vinnapas" 50 V 1, hydrocarbon resin 95 HC 10, HC 20 and HC 30. Polyvinyl ether is also an effective tackifier. Acrylate resins may likewise be used, alone or in mixtures with above-mentioned tackifiers.

A further aspect of the invention relates to a two-layer sheetlike article, more particularly a wound covering, comprising a first layer composed of a foam material, and a second layer as a germ barrier, composed more particularly of a film material, this second layer immediately adjoining a major surface of the first layer, characterized in that, for a pore size of the substantially open-celled foam material in the range from 0.02 mm to 0.2 mm, the material of the second layer has penetrated not more than 0.01 mm into the foam material. A minimal depth of penetration of this kind can be brought about in particular by means of a process as set out in detail above, whereas conventional spray application of polyurethane solutions results in a depth of penetration of at least about 0.05 mm.

An additional aspect of the invention relates to the use of an extrusion process in the production of a film layer directly on a foam wound covering.

Figure 2:
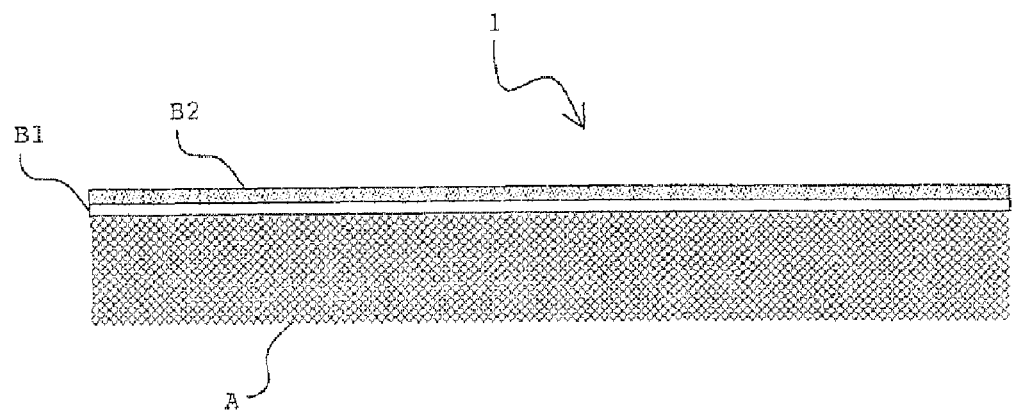
Figure 3:
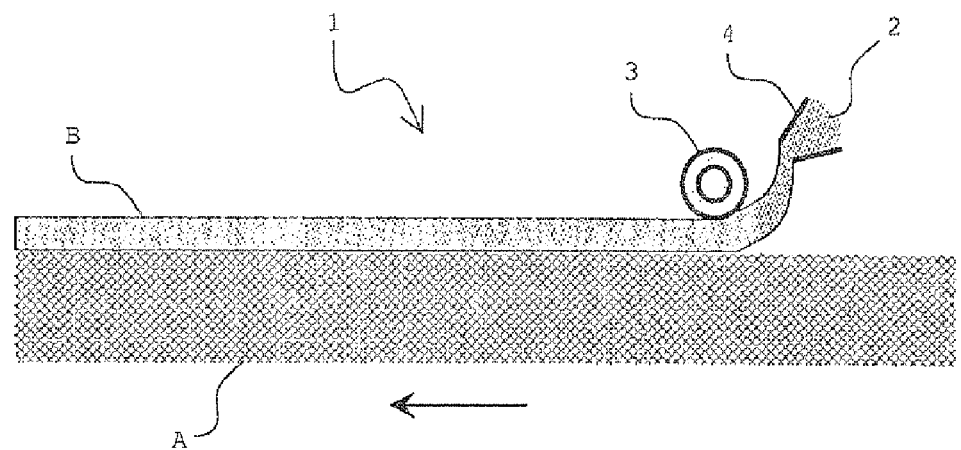
Figure 4:
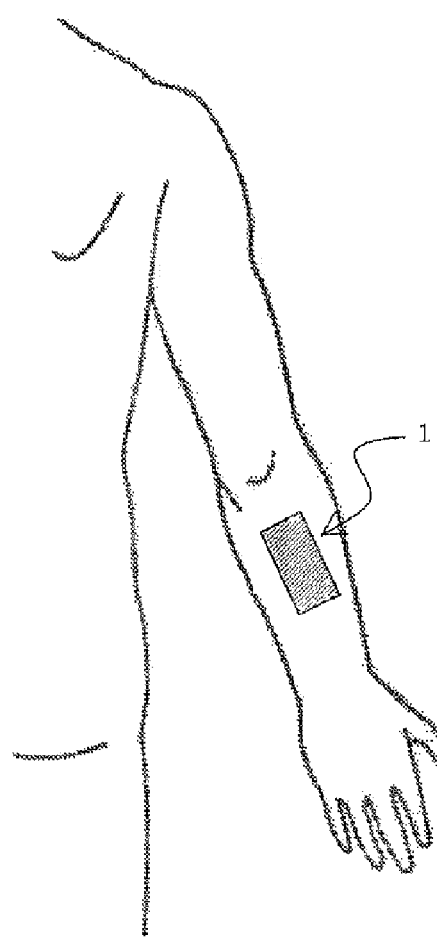

The invention is elucidated below with reference to working examples and figures, without the subject matter of the invention being restricted to these working examples. The figures show:

FIG. 1: wound covering with foam layer and external film;
FIG. 2: wound covering with foam layer and two external film layers;
FIG. 3: production process, diagrammatic;
FIG. 4: wound covering on an arm.

FIG. 1 shows, diagrammatically and in simplified form, an inventive wound covering 1 obtainable by the process described in detail above and illustrated in FIG. 3, and comprising a wound-facing first layer A, composed of a foam material, and a second, germ barrier layer B, composed of a film material. The two layers A and B are joined without an interlayer; in particular there is no adhesive layer between the first layer A and the second layer B. Particularly reliable bonds are obtained if the materials of the first layer A and second layer B are chemically related. Advantageously the first layer A is a hydrophilic polyurethane foam, and layer B is a layer of polyether polyurethane; the similar chemical nature of the two layers allows a particularly stable bond to be achieved.

The embodiment according to FIG. 1 additionally has a substantially uninterruptedly sheetlike layer C for fixing in the wound region, this layer comprising a pressure-sensitive adhesive. A pressure-sensitive adhesive layer of this kind can be applied by methods typical to the art, more particularly by extrusion or transfer coating. The pattern of application of the pressure-sensitive adhesive may of course also be interrupted, should this be necessary in order to ensure a sufficient water vapour transmission rate, or if fixing is desired to the body, for example, only in a marginal region of the wound covering.

FIG. 2 shows an embodiment of an inventive wound covering in which a second layer has been applied to a first layer A composed of a foam material, the second layer comprising the part-layers B1 and B2. Layers B1 and B2 can be produced either together, by means of coextrusion (or sequential extrusion), for example. It is also possible to produce only layer B1 by means of extrusion, with layer B2 being applied sequentially, for example, by spraying. Layer B2 can but need not have been applied areally; in particular, it may also be an imprint, comprising indicia such as manufacturer details, brand names or else cutting lines to make it easier to cut the wound covering to fit on site.

FIG. 3 provides a diagrammatic illustration of an embodiment of the inventive production process, with reference to a wound covering. On a conventional, appropriate extrusion line (not shown in detail), a first layer A of a foam material is conveyed along the arrow direction. In order reliably to ensure conveying of the foam material, it is possible where appropriate to provide a rigid carrier material for the layer A. Via a die 4, typically a slot die, a thermoplastic material is extruded (in this case a thermoplastic polyether polyurethane), typically at a temperature between 150° C. and 240° C., preferably at 180° C. and 220° C. The die 4 in this case has no direct contact with the layer A; instead, material 2 leaves the die in a preformed state and is deposited to a certain extent on the layer A, and thereafter is pressed against the layer A, preferably with a cooled roll 3, in such a way as to form a strong bond between layer A and the layer B formed from the material 2.

FIG. 4 shows a wound covering 1 according to the invention in use, here by way of example as a covering for a wound on an arm. In this plan view, the wound-remote layer B is depicted with diagonal lines. Hidden (in the figure) on the wound-facing side is the layer A, composed of a foam material. The wound covering can be fixed by means, for example, of pressure-sensitive adhesive strips. Preferably, however, additionally or alternatively, the wound covering is fastened with a pressure-sensitive adhesive layer on the wound side, as described above. The size of the wound covering 1 should be chosen appropriate to the size of the particular wound, either through the use of prefabricated wound coverings or by separation (as for example by tearing along perforations), more particularly by cutting to size (for example, along markings preferably printed onto the layer A) of a suitably-sized wound covering from a larger unit.

Wound dressings obtained by the process of the invention were analysed for the strength of the bond between film and foam, and compared with a typical current commercial product. The material used to produce the film layer (layer B) was Pearlthane® D16N85 (manufacturer: Merquinsa), MFI 10 g/10 min at 170° C. (piston weight 21.6 kg), extrusion temperature 205° C.; the foam base used in each case (layer A) is indicated in Table 1. In this connection the following test methods were used:

Test Method 1: Adhesion 5 ml of an aqueous 0.9% NaCl solution are applied to the polyurethane foam side of 100 cm$^2$ (10×10 cm specimen) of the assembly formed from layer A and layer B. The wetted specimens are subsequently stored in a saturated water vapour atmosphere at 40° C. for 24 h. Following the removal of the test specimens, they are cooled to room temperature over 10 minutes. Subsequently the adhesion between polyurethane film and polyurethane foam is assessed qualitatively by hand. For the purpose of comparison, an assessment is made of samples which have not been subjected to hot wet storage. The adhesion found is classified according to a rating system (1=unusable, 2=weak, 3=inadequate, 4=adequate, 5=good, 6=excellent).

Test Method 2: Imperviousness 5 ml of an aqueous 0.9% NaCl solution stained with 0.1% of methylene blue are applied to the polyurethane foam side of 100 cm$^2$ (10×10 cm specimen) of the assembly formed from layer A and layer B. After 1 hour (room temperature) the imperviousness on the polyurethane film side (layer B) is assessed visually. The imperviousness found is classified according to a rating system (1=unusable, 2=weak, 3=inadequate, 4=adequate, 5=good, 6=excellent).

The results obtained are indicated in Table 1:

TABLE 1

Assessment of adhesion and imperviousness of inventive wound dressings.

| PU film extruded on: | Vivo MCF 03 (Corpura B.V.) | Foam 3014 (Polymer Health Technology) | Reference specimen 3M Foam Dressing (Art. 90601) |
|---|---|---|---|
| Adhesion between foam and film (blank value) | 6 | 6 | 5 |
| Adhesion between foam and film after 24 h of humid storage at 40° C. | 5 | 5 | 3-4 |
| Imperviousness after 1 hour | 6 | 6 | 6 |

It is apparent that the strength of the bond between layer A (foam) and layer B (film) in the case of the wound dressings of the invention and/or as a result of the production process of the invention is improved for a wound dressing of this kind under typical service loading.

Pressure-sensitive adhesives which have proved to be particularly advantageous, more particularly for use in layer C (cf. FIG. 1), are polyurethane pressure-sensitive adhesives based on isophorone diisocyanate and/or modified isophorone diisocyanate. Particular preference is given to compositions which comprise:

A polymer obtainable by polymerizing at least polyols having 2 to 6 hydroxyl groups, more particularly polyether polyols having OH numbers of 20 to 112 and an ethylene oxide (EO) content of ≧10% by weight, preferably 10% to 40% by weight, more preferably 10% to 20% by weight; and isophorone diisocyanate and/or modified isophorone diisocyanate;

further comprising:

sterically hindered bismuth compounds soluble in the polyol or polyols, more particularly in the polyether polyol or polyols of a), more particularly bismuth(III) carboxylates based on carboxylic acids having 2 to 18 C atoms, preferably Bi(III) neodecanoate; and also optionally, antioxidants.

With particular preference the pressure-sensitive adhesive composition further exhibits:

a product of the functionalities of components a) and b) of at least 5.2; and/or a fraction of component c) of 0.005% to 0.5% by weight, based on component a); and/or a fraction of antioxidants d) in the range from 0.1% to 1% by weight, based on component a); and/or a ratio of NCO groups of component b) to the NCO-reactive functional groups of component a) in the range from 0.10 to 0.90.

Particularly preferred pressure-sensitive adhesives have, for example, the following compositions (amounts in % by weight):

|  | PSA1: | PSA2: |
| --- | --- | --- |
| Resin | Resin | Resin |
| Polyether polyol (Levagel VPKA 8732; Bayer); OHN 35 | 99.4 | — |
| Trifunctional polypropylene ether polyol (Desmophen 5034 BT; Bayer) | — | 99.5 |
| DABCO 33LV (Air Products) | — | 0.5 |
| Bi(III) catalyst (in this case: neodecanoate; Coscat 83; Cosan Chemical Corporation) | 0.4 | — |
| Stabilizer (in this case: tocopherol) | 0.2 | — |
| Curing agent | Resin: curing agent mixing ratio | Resin: curing agent mixing ratio |
| Prepolymer based on HDI (Desmodur E305; Bayer); NCO content about 13% | — | 2.48:1 |
| Aliphatic prepolymer based on IPDI (Desmodur VP LS 2371); NCO content about 3.8% | 2.34:1 | — |

The properties of this composition were determined as follows:

Water Vapour transmission Rate (DIN EN 13726-2:2002; determined on "Nonwoven (Union)" carrier material):

3304 g/m$^2$/24 h for a coatweight of 100 g/m$^2$ (PSA1);

3654 g/m$^2$/24 h for a coatweight of 63.5 g/m$^2$ (PSA2; on the assumption of water vapour transmission rate decreasing linearly with increasing layer thickness, a water vapour transmission rate of 2320 g/m$^2$/24 h results for a coatweight of 100 g/m$^2$ in comparison to PSA1).

Water Absorption (DIN EN 13726-1:2002):

<10 g/m$^2$/24 h (<2% by weight) for a PSA layer thickness of 0.15 mm (PSA1);

25 g/m$^2$/24 h (4.3% by weight) for a PSA layer thickness of 0.15 mm (PSA2).

The invention claimed is:

1. Wound covering being at least two-layered, said covering having
    a first layer composed of a foam material, exhibiting a first major surface and a second major surface;
    a second layer as a germ barrier, more particularly composed of a film material, this second layer directly adjoining the first major surface of the first layer; and
    a pressure-sensitive adhesive on the second major surface of the first layer, the pressure-sensitive adhesive comprising a polymer which is obtainable by polymerizing at least one isocyanate component with at least one diol or polyol component;
    wherein the pressure-sensitive adhesive is not allowed to penetrate the first layer through to the first major surface, and
wherein a layer of the pressure-sensitive adhesive has
    a water vapor transmission rate of ≧2000 g/m$^2$/24 h for a basis weight of the pressure-sensitive adhesive of approximately 100 g/m$^2$ or
    a water absorption of <5% by weight.

2. Wound covering according to claim 1, wherein the material of the second layer does not penetrate more than 0.01 mm into the foam material.

3. Process for producing an at least two-layered, substantially uninterruptedly sheetlike wound covering according to claim 1, said process comprising the following steps:
    (a) providing the foam material of the first layer;
    (b) areally applying at least one thermoplastic material to the major surface of the foam material at a temperature above the softening temperature of the thermoplastic material, and solidifying the material to give the second layer, wherein the first layer, composed of a foam material, is not being embedded into the pressure-sensitive adhesive layer; and
    (c) at least partially applying a pressure-sensitive adhesive onto the second major surface of the first layer, the pressure-sensitive adhesive comprising a polymer which is obtainable by polymerizing at least one isocyanate component with at least one diol or polyol component,
wherein the pressure-sensitive adhesive is not allowed to penetrate the first layer through to the first major surface, and
wherein a layer of the pressure-sensitive adhesive has
    a water vapor transmission rate of ≧2000 g/m$^2$/24 h for a basis weight of the pressure-sensitive adhesive of approximately 100 g/m$^2$ or
    a water absorption of <5% by weight.

4. Process according to claim 3, wherein a polyurethane foam is provided as the first layer.

5. Process according to claim 3, wherein the first layer is hydrophilic.

6. Process according to claim 3, wherein the foam material of the first layer is open-celled.

7. Process according to claim 3, wherein the at least one material in step b) is extruded onto the foam material in such a way as to form a second layer having a thickness between 5 μm to 500 μm.

8. Process according to claim 7, wherein the extrusion of the at least one material in step b) takes place at a temperature in the range between 150° C. and 240° C.

9. Process according to claim 7, wherein after extrusion of the material in step b), the extrudate is pressed against the first layer by means of a cooled roll.

10. Process according to claim 3, wherein two layers are produced in step b).

11. Process according to claim 3, wherein the at least one material in step b) is foamed during and/or after the areal application.

12. Process according to claim 3, wherein the material in step b) is a thermoplastic polyurethane material.

13. Process according to claim 3, wherein an isocyanate component is used which is selected from the group consisting of MDI; TDI; XDI; NDI; phenylene diisocyanate; dicyclohexylmethane diisocyanate; butane 1,4-diisocyanate; tetramethoxybutane 1,4-diisocyanate; hexane 1,6-diisocyanate; ethylene diisocyanate; 2,2,4-trimethylhexamethylene diisocyanate; ethylethylene diisocyanate; dicyclohexylmethane diisocyanate; 1,4-diisocyanatocyclohexane; 1,3-diisocyanatocyclohexane; 1,2-diisocyanatocyclohexane; 1,3-diisocyanatocyclopentane; 1,2-diisocyanatocyclopentane; 1,2-diisocyanatocyclobutane; 1-isocyanatomethyl-3-isocyanato-1,5,5-trimethylcyclohexane (isophorone diisocyanate); 1-methyl-2,4-diisocyanatocyclohexane; 1,6-diisocyanato-2,2,4-trimethylhexane; 1,6-diisocyanato-2,4,4-trimethylhexane; 5-isocyanato-1-(2-isocyanatoeth-1-yl)-1,3,3-trimethylcyclohexane; 5-isocyanato-1-(3-isocyanatoprop-1-yl)-1,3,3-trimethylcyclohexane; 5-isocyanato-1-(4-isocyanatobut-1-yl)-1,3,3-trimethylcyclohexane; 1-isocyanato-2-(3-isocyanatoprop-1-yl)-cyclohexane; 1-isocyanato-2-(2-isocyanatoeth-1-yl)-cyclohexane; 2-heptyl-3,4-bis-(9-isocyanatononyl)-1-pentyl-cyclohexane; norbornane diisocyanatomethyl; chlorinated, brominated, aliphatic or alicyclic diisocyanates containing sulphur or containing phosphorus; and derivatives of these diisocyanates, more particularly dimerized or trimerized types; and also mixtures of these isocyanates.

14. Process according to claim 3, wherein a diol or polyol component is used which is selected from the group consisting of oxyalkyl polymers, preferably polyether polyols having 2, 3, 4, 5 or 6 hydroxyl groups, OH numbers of 20 to 112 and an ethylene oxide content of 10% by weight, preferably of 10-40% by weight, more preferably of 10-20% by weight, in each case having an average molecular weight in the range from about 600 g/mol to about 12 000 g/mol;
poly(meth)acrylic polyols;
polyester polyols, preferably having an average molecular weight in the range from about 200 g/mol to about 10 000 g/mol; polyolefin polyols; polythiol polyols; polyamine compounds; and also mixtures thereof.

15. Process according to claim 3, the diol or polyol component having a glass transition temperature Tg in the region of below about 20° C., preferably below about 0° C., more preferably below about −10° C.

16. Process according to claim 3, the polyurethane pressure-sensitive adhesive comprising a polymer which is obtainable by polymerizing
isophorone diisocyanate or a modified isophorone diisocyanate with
at least one polyether polyol.

17. Process according to claim 3, wherein polyurethane prepolymers are used.

* * * * *